US007705144B2

(12) United States Patent
Holmes

(10) Patent No.: US 7,705,144 B2
(45) Date of Patent: Apr. 27, 2010

(54) DYES OF IMPROVED OPTICAL BRIGHTNESS AND/OR FLUORESCENCE AND COMPOSITIONS CONTAINING THEM

(76) Inventor: Andrea E. Holmes, 1014 Boswell Ave., Crete, NE (US) 68333

(*) Notice: Subject to any disclaimer, the term of this patent is extended or adjusted under 35 U.S.C. 154(b) by 126 days.

(21) Appl. No.: 11/863,475

(22) Filed: Sep. 28, 2007

(65) Prior Publication Data

US 2009/0083911 A1 Apr. 2, 2009

(51) Int. Cl.

| | |
|---|---|
| ***C07D 413/00*** | (2006.01) |
| ***C07D 413/14*** | (2006.01) |
| ***C07D 413/10*** | (2006.01) |

(52) U.S. Cl. ...................... 544/113; 544/112; 544/194; 8/688; 8/636; 8/662

(58) Field of Classification Search .................... 8/506, 8/648

See application file for complete search history.

(56) References Cited

U.S. PATENT DOCUMENTS

| | | | | |
|---|---|---|---|---|
| 6,143,280 | A | 11/2000 | Pike et al. | |
| 6,630,019 | B2 | 10/2003 | Pike et al. | |
| 6,753,002 | B2 | 6/2004 | George et al. | |
| 7,150,764 | B2 | 12/2006 | Plos et al. | |
| 2005/0183211 | A1* | 8/2005 | Samain et al. | 8/405 |
| 2007/0183992 | A1 | 8/2007 | Dumousseaux et al. | |

FOREIGN PATENT DOCUMENTS

| | | | |
|---|---|---|---|
| EP | 1 298 126 | A1 | 2/2003 |
| JP | 2006-249012 | | 9/2006 |
| WO | 2006/010728 | A1 | 2/2006 |
| WO | 2006/021527 | A1 | 3/2006 |

OTHER PUBLICATIONS

EIC Structure Search, completed by STIC on Dec. 29, 2008.*

* cited by examiner

*Primary Examiner*—Harold Y Pyon
*Assistant Examiner*—Katie Hammer
(74) *Attorney, Agent, or Firm*—McKee, Voorhees & Sease, P.L.C.

(57) ABSTRACT

Preparing dyes suitable for cosmetic use that start with known dyes and link them, for example, with 1,3,5 triazine to bulky organic groups that control solubility.

4 Claims, No Drawings

DYES OF IMPROVED OPTICAL BRIGHTNESS AND/OR FLUORESCENCE AND COMPOSITIONS CONTAINING THEM

FIELD OF THE INVENTION

The invention relates to dyes that impart optical brightness, color purity, and/or fluorescence for use in applications such as cosmetic and toiletry formulations. It also relates to methods of making them. More specifically, the new dyes of controlled solubility and stability in cosmetic formulations and methods to making the dyes and cosmetic compositions containing them.

BACKGROUND OF THE INVENTION

There is a need for dyes which have controlled solubility which would then allow their incorporation into cosmetic vehicles, without having them leech onto the other components of the formulation or emulsion, which could alter their optical properties. For example, the problem with many food dyes for use in cosmetics is that they are water soluble, which limits their use in cosmetics because they dissolve in perspiration and run.

Dyes are historically among the most widely used industrial chemicals, with applications for food, cosmetics, toiletries, and textile industries, to name a few. They impart a visual stimulus to consumers, and offer an enhanced psychological impact. While this is a mature field, there are still inherent problems associated with many dyes for cosmetic use due to their chemical nature. For instance, iron oxide is the primary colorant of rouge makeup, despite the availability of many organic dyes and pigments. The reason for this is many dyes are comprised of conjugated chromophores, which tend to aggregate, causing non-ideal color changes such as dullness, loss of color purity, and fluorescence quenching. Iron oxide on the other hand is stable. Many food dyes and D&C dyes that might therefore be considered for use are water soluble, which limits their use in cosmetics because they may dissolve in perspiration causing the cosmetic to run or leech out. There have been previous efforts to make pigments from water soluble materials that potentially migrate. For example, U.S. Pat. No. 6,630,019 shows mixing aluminum hydroxide with calcium phosphate slurry and then applying an FD&C dye mix. As used herein "FD&C" dyes and "D&C" dyes means any dye listed in Title 21, Part 82 of the Code of Fair Regulations, the content of which is hereby incorporated by reference. For example, U.S. Pat. No. 6,143,280 adheres FD&C dyes to silica and depositing alumina in the pores of the silica in order to resist dye migration.

Other techniques involve encapsulating dyes in order to prevent aggregation and to maintain the desirable spectral properties of the dye. For example, International Publication No. WO2006010728 of Feb. 2, 2006, describes the use of polymer microparticles of fluorescent whitening agents for use in cosmetics. Alternatively, large macrocycles such as cyclodextrins have been used to encapsulate chromophores non-covalently, and are commonly used as an additive when dyeing fabrics to enhance brightness. In these instances the dye and macrocycle form an inclusion complex; however only a certain number of dyes will fit in the cavity of the cyclodextrin. JP2006249012 describes fluorescent cosmetics by using molecularly encapsulated dyes, non-covalently bonded.

U.S. Pat. No. 7,150,764 of Dec. 19, 2006 describes the use of water-soluble fluorescent dyes and an insoluble conditioning agent for use in dyeing keratin fibers, whereas U.S. Pat. No. 6,753,002 of Jun. 22, 2004 teaches the use of fluorescent mineral powders with cosmetically acceptable vehicles to solve stability problems caused by moisture. Triazine-stilbene fluorescent brighteners have been reported (Dyes and Pigments, 2005, 63), as well as naphthol-triazine compounds as UV light absorbers as inhibitors for plastic degradation (EP1298126).

In all of the above approaches, to overcome the problem of stability to make cosmetic compositions that are cosmetically acceptable the approach has been adding things to the formulation to protect color; this changes the properties of the formulation and sacrifices some cosmetic elegance, as well increases expense. Thus, if wholly insoluble materials are used, caking can become a problem. If, on the other hand, encapsulation is used, sacrifice of color appearance may occur. These problems have limited the ability of any of these techniques to work easily with all FD&C and D&C dyes for cosmetics.

Accordingly, it can be seen that there is still a need for controlling dye solubility and for a methodology that meets current safety standards for each application, while allowing easy to manufacture dyes, which themselves have their properties controlled such that they are adaptable to current formularies while being cosmetically elegant, i.e., formulations that are stable, do not run or migrate, and which do not have color changes, such as dullness or loss of color when in use.

It is a primary object of the present invention to fulfill the above needs.

Another object of the present invention is to modify dyes themselves so that water solubility or lack of solubility are carefully controlled resulting in "tailor made" molecules, favorable for the cosmetic use in question. As a result, many FD&C and D&C dyes can now be used, where they could not otherwise be.

BRIEF SUMMARY OF THE INVENTION

This invention covalently links industrial dyes such as FD&C and D&C dyes to large organic moieties in order to control solubility, and at the same time allow the dye to have its ordinary photoluminescence properties (fluorescents and phosfluorescents). The dye is linked to the bulky organic constituent through a covalent linker such as the 1,3,5 triazine moiety. In its broadest sense, the invention relates to molecular dyes that address these issues, with the given formula X-L-(Y)z, with X, L the linker or bridge, Y and Z defined as hereafter provided. A more specific description follows.

DETAILED DESCRIPTION OF A PREFERRED EMBODIMENT

The dye "X" represents a plurality of common industrial dyes such as optical brighteners, food dyes, and D&C dyes. Optical brighteners are chromophores that typically absorb UV light (200-400 nm) and emit blue light in the visible spectrum. Exemplary molecules include but are not limited to derivatives of stilbene, biphenyl, naphthalene, and anthracene. Where X is a food dye or a D&C dye, the absorbance is at the visible region (400-800 nm). Exemplary molecules may be found in the FD&C Handbook, and are chosen accordingly by their chemical and spectral properties by a person skilled in the formulation art of cosmetics. For example, an FD&C dye may be chosen for its low toxicity, as well as its color for a cosmetic formulation. An "X" dye that appears green may be chosen to cover skin redness such as rosacea. Preferred are FD&C and D&C dyes because both are approved non-toxic dyes. Solubility is controlled thereafter in accord with this invention through the linker moiety and the covalent bond to the bulky organic moiety of "Y".

A general introduction and overview of organic colorants, i.e., "x" in our case is provided in, W. Herbst, K. Hunger; Industrial Organic Pigments, $2^{nd}$ Ed, VCH Verlagsgesellschaft, Weinheim, 1997, and a brief overview of fluorescent colorants in particular is given in B. M. Krasovitskii, B. M. Bolotin; Organic Luminescent Materials, 1988, VCH Weinheim.

A variety of colorants, from many chemical classes, show solid and/or solution state fluorescence. In principle, absorption of light energy excites molecules in these colored materials to their excited states. When deactivation of these excited states takes place via radiative decay, resulting in emission of light at a longer wavelength to the absorbed light, then fluorescence is said to have occurred. To the observer, this effect provides an unusual brilliance to the colorant, beyond that of traditional colorants employed in cosmetics. This brilliance is caused by both the ultraviolet and short-wavelength components of visible light.

Typical fluorescent colorants (both pigments and dyes), other than traditional fluorescent whitening agents, can be used in the present invention. They include for example, but are not limited to, materials of the following chemical classes:

a) perylene derivatives of the general formulae (i)

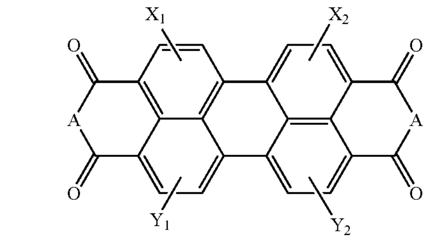

and (Ia)

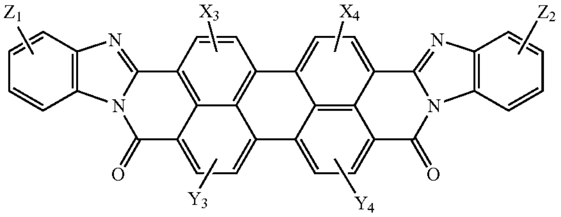

or its regioisomer, wherein or its regioisomer, wherein a) is O, N—H, N-alkyl or N-aryl and $X_1$, $X_2$, $X_3$, $X_4$, $Y_1$, $Y_2$, $Y_3$, $Y_4$, $Z_1$, $Z_2$ are independently halogen, O-alkyl or O-aryl, for example Pigment Red 2:24:

b) fluoresceins of the general formula (II)

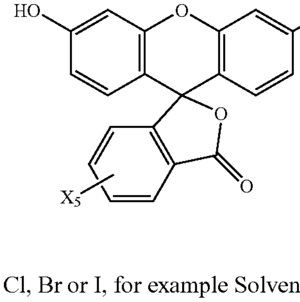

wherein $X_5$ is Cl, Br or I, for example Solvent Yellow 94, Cl 45350;

c) rhodamines of the general formula (III)

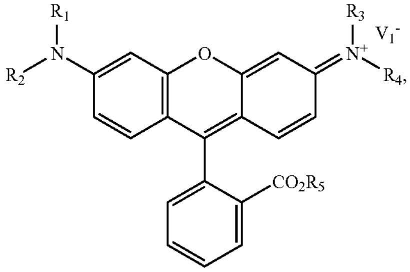

wherein the $R_1$, $R_2$, $R_3$, $R_4$, $R_5$ groups are independently H or $C_1$-$C_{12}$alkyl, and $V_1$ is Cl, Br or I, for example Basic Red 1, Cl 45160;

d) pyronines of the general formula (IV)

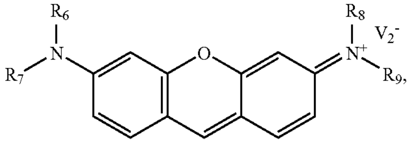

wherein $R_6$, $R_7$, $R_8$ and $R_9$ groups are independently H or $C_1$-$C_{12}$alkyl, and $V_2$ is Cl, Br or I, for example Pyronin G, Cl 45005;

e) naphthalic anhydride derivatives of the general formula (V)

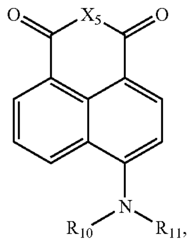

wherein $X_5$ is O, N—H, N-alkyl or N-aryl and $R_{10}$ and $R_{11}$ are independently H, alkyl or aryl, for example Solvent Yellow 43;

f) benzoxanthenes and benzthioxanthenes of the general formulae regioisomer, wherein $X_6$, $X_7$ and $X_8$ are independently O-alkyl, O-aryl or halogen, $Y_5$ is O, N—H, N-alkyl or N-aryl and $Z_3$ and $Z_4$ are independently O or S, for example Solvent Yellow 98;

g) benzanthrone derivatives of the general formula (vi)

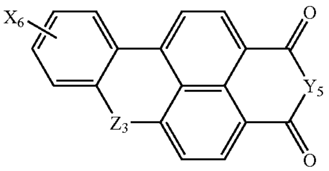

and

-continued (viA)

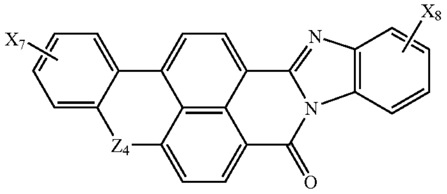

or its regioisomer, wherein $X_6$, $X_7$ and $X_8$ are independently O-alkyl, O-aryl or halogen $Y_5$ is O, N—H, N-alkyl or N-aryl and $Z_3$ and $Z_4$ are independently C or S, for example Solvent Yellow 98;

g) benzanthrone derivatives of the general formula (VII)

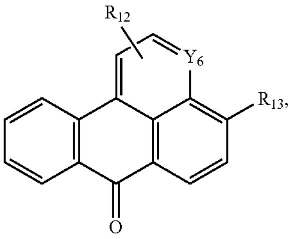

wherein $Y_6$ is C or N and $R_{12}$ and $R_{13}$ are independently halogen, alkoxy, amino or alkylamino and when $Y_6$ is C, $Y_6$ plus $R_{13}$ can form a 6-membered ring, optionally fused to an arylene group, for example Solvent Orange 63 of the formula (VIIa)

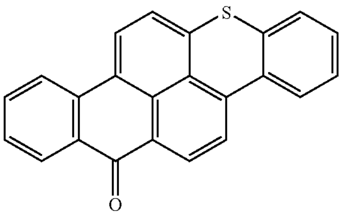

h) coumarins of the general formula (VIII), wherein (VIII)

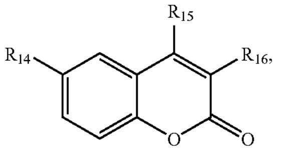

wherein $R_{14}$ is H, alkoxy, amino or alkylamino, and $R_{15}$ and $R_{16}$ are independently H, alkyl or aryl; for example solvent yellow 160;

i) isoindolo-[2,1-a]-benzimidazolone derivatives of the general formula (IX)

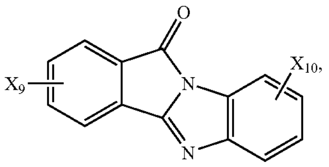

wherein $X_9$ and $X_{10}$ and are independently hydrogen or halogen, for example 1,2,3,4,7-pentachloro-11H-isoindolo-[2,1-a]-benzimidazol-11-one of the formula (IXa)

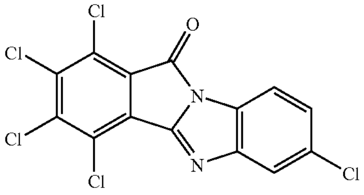

j) diphenyl maleimides of the general formula (X)

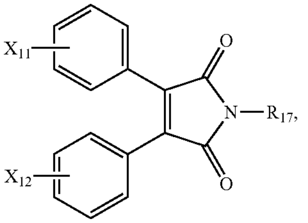

wherein $R_{17}$ is optionally substituted alkyl or aryl and $X_{11}$ and $X_{12}$ are independently H, alkyl, aryl, O-alkyl, O-aryl or halogen;

k) azo pigments of the general formula (XI)

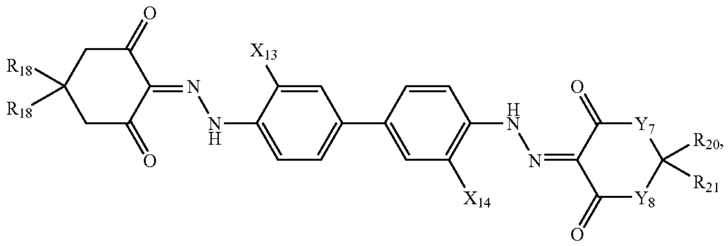

wherein $X_{13}$ and $X_{14}$ are independently halogen or alkoxy, $Y_7$ and $Y_8$ are independently $CH_2$ or O and $R_{18}$, $R_{19}$, $R_{20}$ and $R_{21}$ are independently optionally substituted alkyl or aryl;

l) diketopyrrolo[3,4-c]pyrroles (abbreviated to DPP) of the general formula (XII)

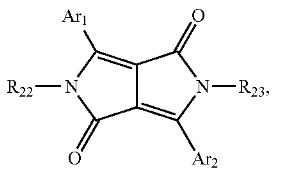

wherein $Ar_1$ and $Ar_2$ are aryl radicals and $R_{22}$ and $R_{23}$ are independently optionally substituted alkyl or aryl radicals;

m) condensation products of aromatic or heteroaromatic aldehydes with barbituric acid derivatives, and mixtures thereof.

Preferred classes of fluorescent colorants for the present invention are those having a yellow and/or reddish blue. They include condensation products of N,N'-di($C_1$-$C_8$alkyl) amino-benzaldehyde and barbituric acid such as those disclosed in Chem. Berichte, 39, 2166, (1906), perylene derivatives of the formula (I) and (Ia) such as those disclosed in DE 42 25 0317, diphenyl maleimides of the formula (X) such as those disclosed in U.S. Pat. No. 6,508,957, benzoxanthenes and benzthioxanthenes of the formulae (VI) and (VIa) such as those disclosed in EP 1 172 418 A2 and corresponding U.S. Pat. Nos. 6,462,128 and 6,559,306 and similar compounds, N,N'-disubstituted DPPs of the formula (XII) and the isoindolo-[2,1-a]-benzimidazolone of the formula (IXa) and

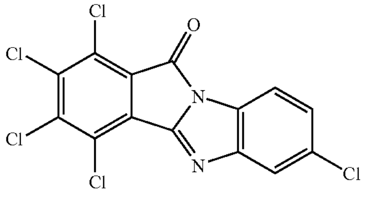

and mixtures thereof, wherein the substituents in the formulae are as defined above.

In one preferred embodiment, the colorant is an aqueous solution of a water-soluble dye. Such dyes may include FD&C Blue No. 11, FD&C Blue No. 12, FD&C Green No. 13, FD&C Red No 13, FD&C Red No. 140, FD&C Yellow No. 15, FD&C Yellow No. 16, D&C Blue No 14, D&C Blue No. 19; D&C Green No. 15, D&C Green No. 16, D&C Green No. 18, D&C Orange No. 14, D&C Orange No. 15, D&C Orange No. 110, D&C Orange No. 111, D&C Orange No. 117, FD&C Red No. 14, D&C Red No. 16, D&C Red No. 17, D&C Red No. 18, D&C Red. No. 19, D&C Red No. 117, D&C Red No. 119, D&C Red. No. 121, D&C Red No. 122, D&C Red No. 127, D&C Red No. 128, D&C Red No. 130, D&C Red No. 131, D&C Red No. 134, D&C Red No. 139, D&C Red No. 140, D&C Violet No. 12, D&C Yellow No. 17, Ext. D&C Yellow No. 17, D&C Yellow No. 18, D&C Yellow No. 111, D&C Brown No. 11, Ext. D&C Violet No. 12, D&C Blue No. 16 and D&C Yellow No. 110.

The above dyes are well known, commercially available materials with their chemical structure being described, e.g., in 21 C.F.R. Part 74 (as revised Apr. 1, 1988) and in the CTFA Cosmetic ingredient Handbook, (1988), published by the Cosmetics, Toiletry and Fragrances Association, Inc. These publications are incorporated herein by reference.

The certified dyes can be water-soluble or, preferably, lakes thereof. Lakes are organic pigments prepared by precipitating a soluble dye on a reactive or absorbent stratum, which is an essential part of the pigment's composition. Most hikes are aluminum barium or calcium derived. These insoluble pigments are used mostly in makeup products, either as powders or liquids, when a temporary color is desired that won't stain the skin (as oil-soluble dyes tend to do). The lakes are used in these products along with inorganic colors.

The following tables list currently available dyes and colorants approved for use in food, drugs and/or cosmetics. The selected colorant for use herein is preferably selected from the following exemplary lists.

TABLE 1

| Dyes certified for use in foods, drugs, cosmetics (FDC colors) | | |
|---|---|---|
| FD&C Blue No. 1 | FD&C Green No. 3 | FD&C Red No. 4 |
| FD&C Red No. 40 | FD&C Yellow No. 5 | FD&C Yellow No. 6 |

TABLE 2

| Dyes certified for topically applied drugs and cosmetics | | |
|---|---|---|
| Ext. DC Violet No. 2 | Ext. D&C Yellow No. 7 | Ext. D&C Violet No. 2 |
| D&C Brown No. 1 | FD&C Red No. 4 | D&C Red No. 17 |
| D&C Red No. 31 | D&C Red No. 34 | D&C Red No. 39 |
| D&C Violet No. 2 | D&C Blue No. 4 | D&C Green No. 6 |
| D&C Green No. 8 | D&C Yellow No. 7 | D&C Yellow No. 8 |
| D&C Orange No. 11 | D&C Orange No. 4 | D&C Orange No. 10 |

TABLE 3

| Dyes Certified for drugs and foods only | | |
|---|---|---|
| D&C Blue No. 4 | D&C Brown No. 1 | D&C Green No. 5 |
| D&C Green No. 6 | D&C Green No. 8 | D&C Orange No. 4 |
| D&C Orange No. 5 | D&C Orange No. 10- | D&C Orange No. 11 |
| D&C Red No. 6 | D&C Red No. 7 | D&C Red No. 17 |
| D&C Red No. 21 | D&C Red No. 22 | D&C Red No. 27 |
| D&C Red No. 28 | D&C Red No. 30 | D&C Red No. 31 |
| D&C Red No. 33 | D&C Red No. 34 | D&C Red No. 36 |
| D&C Violet No. 2 | D&C Yellow No. 7 | D&C Yellow No. 8 |
| D&C Yellow No. 10 | D&C Yellow No. 11 | |

Some color additives are exempt from certification and permanently listed for cosmetic use, including aluminum powder, annatto, bronze powder, caramel, carmine, beta-carotene, dihydroxyacetone, disodium EDTA-copper, guanine (pearl essence), guaiazulene (azulene), mica, pyrophyllite, silver (for coloring fingernail polish), and the ultramarines (blue, green, pink, red & violet).

They may also include fluorescent substances that are derivatives of 4,4'-diaminostilbene and 4,4'-diaminostilbene-2,2'-disulfonic acids, 4,4'-dibenzofuranyl-biphenyls, 4,4'-(diphenyl)-stilbenes, 4,4'-distyryl-biphenyls, 4-phenyl-4'-benzoxazolyl-stilbenes, stilbenzyl-naphthotriazoles, 4-styryl-stilbenes, bis-(benzoxazol-2-yl) derivatives, bis-(benzimidazol-2-yl) derivatives, coumarins, pyrazolines, naphthalimides, triazinyl-pyrenes, 2-styryl-benzoxazole or -naphthoxazoles, benzimidazole-benzofurans and oxanilides.

Compositions for dyeing fibers such as keratinous fibers may incorporate dyes that are not D&C dyes (i.e. nailpolish compositions).

The choice of the fluorescent whitening agent used in the present invention is not critical. It can be oil or water soluble and may be selected from a wide range of chemical classes such as 4,4'-bis-(triazinylamino)-stilbene-2,2'-disulfonic acids, 4,4'-bis-(triazol-2-yl)stilbene-2,2'-disulfonic acids, 4,4'-dibenzofuranyl-biphenyls, 4,4'-(diphenyl)-stilbenes, 4,4'-distyryl-biphenyls, 4-phenyl-4'-benzoxazolyl-stilbenes, stilbenzyl-naphthotriazoles, 4-styryl-stilbenes, bis-(benzoxazol-2-yl) derivatives, bis-(benzimidazol-2-yl) derivatives, coumarins, pyrazolines, naphthalimides, triazinyl-pyrenes, 2-styryl-benzoxazole or -naphthoxazoles, benzimidazole-benzofurans and oxanilides. Mixtures thereof of fluorescent whitening agents of the same or different chemical classes may be employed.

Microcapsules wherein the fluorescent whitening agent is selected from the group consisting of 4,4'-bis-(triazinylamino)-stilbene-2,2'-disulfonic acids, 4,4'-dibenzofuranyl-biphenyls and mixtures thereof are especially preferred.

Examples of fluorescent substances include of derivatives of stilbene and 4,4'-diaminostilbene; derivatives of benzene and biphenyl; derivatives of pyrazines; derivatives of bis(benzoxazol-2-yl); coumarins; carbostyrils; naphthalimides, s-triazines; and pyridotoriazols.

Examples of the fluorescent brightener are stilbene derivatives, styryl derivatives of benzene and biphenyl, bis(benzazol-2-yl) derivatives, derivatives of coumarin, carbostyryl, naphthalimide and dibenzothiophene-5,5-dioxide, pyrene derivatives, and pyridotriazole. Among them, derivatives of 4,4'-diaminostilbene-2,2'-disulfonic acid, 4-methyl-7-diethylaminocoumarin, 2,5-bis(5-tert-butyl-2-benzoxazolyl) thiophene and the like are preferred.

Linking of X and Y is achieved by covalent bonds of a linker moiety (L), such as 1,3,5 triazine, and triazole. Direct reaction is applicable for dye molecules containing reactive groups such as primary and secondary amines and alcohols. Where functional groups that exhibit slow reactivity are present, these may be converted chemically to more reactive groups, for example the conversion of carboxylic acids to more reactive acyl chlorides, and the conversion of sulfonic acids to more reactive sulfonyl chlorides. The appropriate chemical derivative of preferred FD&C or D&C dyes may be chosen by a person skilled in the art of cosmetic formulation.

Preferentially, the linking of X and Y is through reaction with cyanuric chloride, which allows temperature-controlled substitution of the chlorine atoms. This allows the addition of 1 or 2 Y, or 1 Y and a second chemical group such as an alkyl chain or an alkylammonium group, or 2 Y of different composition, or 1 Y and leaving the last chlorine atom to remain to allow a reactive site on the dye. Preferentially, the addition is through nucleophilic attack of the triazine ring by N or O.

The linking molecule does not have to be 1,3,5 triazine although it is preferred. For example, 2,3-dichloroquinoxaline also works. Others would work as well. However, 1,3,5 triazine is preferred because it is easily commercially available and its use is very common in dyes with chemistry is easy to work with.

Where Linker is Ar I, Ar II, nitrogen, carbon, or silicon as defined below.

Ar I and Ar II are independently a substituted or unsubstituted mono- or bicyclic ring, said rings optionally substituted with 0 to about 3 R groups.

Preferably, Ar I is a substituted or unsubstituted mono- or bicyclic aryl or heteroaryl ring system of about 5 to about 12 atoms and where each monocyclic ring may contain 0 to about 3 hetero atoms, and each bicyclic ring may contain 0 to about 4 hetero atoms selected from N, O and S provided said hetero atoms are not vicinal oxygen and/or sulfur atoms and where the substituents may be located at any appropriate position of the ring system and are described by R.

Ar II may be as described for Ar I or at least one ring is a substituted or unsubstituted saturated carbocyclic of about 3 to about 7 atoms where each monocyclic ring may contain 0 to about 2 hetero atoms, and each bicyclic ring may contain 0 to about 4 hetero atoms selected from N, O and S provided said hetero atoms are not vicinal oxygen and/or sulfur atoms and where the substituents may be located at any appropriate position of the ring system and are described by R.

Preferred Ar I and Ar II monocyclic aryl or heteroaryl rings include substituted or unsubstituted benzene, pyrrole, thiophene, furan, thiazole, imidazole, pyrazole, 1,2,4-triazol, 1,2,3-triazole, pyridine, 2(1H)-pyridone, 4(1H)-pyridone, pyrazine, pyrimidine, pyridazine, isothiazole, isoxazole, s-triazine, oxazole and tetrazole.

Preferred Ar II carbomonocyclic rings include substituted and unsubstituted cycloalkanes such as cyclopentane, cyclohexane, cycloheptane and partially unsubstituted cycloalkanes such as cyclopent-1-ene and heteromonocyclic rings such as piperidine, piperazine, morpholine and pyrrolidine.

Preferred Ar I and Ar II bicyclic rings include substituted and unsubstituted bicyclic aryl and heteroaryl rings such as naphthalene, naphthyridine, benzofuran, benzothiophene, indole, 1H-indazole, indoline, benzopyrazole, 1,3-benzodioxole, benzoxazole, purine, coumarin, chromone, quinoline, isoquinoline, benzimidazole, quinazoline, pyrido[2,3-b] pyrazine, pyrido[3,4-b]pyrazine, pyrido[3,2-c]pyridazine, pyrido[3,4-b]-pyridine, pteridine, 2(1H)-quinolone, 1(2H)-isoquinolone, 1,4-benzisoxazine, benzothiazole, quinoxaline, quinoline-N-oxide, isoquinoline-N-oxide, quinoxaline-N-oxide, quinazoline-N-oxide, benzoxazine, phthalazine, or cinnoline.

Preferred Ar II carbobicyclic rings include substituted and unsubstituted bicycloalkanes such as tetralin and adamantane and preferred heterobicyclic rings such as chroman and indoline.

Preferred R substituents other than hydrogen include alkyl, alkenyl, phenyl, aralkyl, aralkenyl, hydroxy, hydroxyalkyl, alkoxy, alkoxyalkyl, aralkoxy, acyloxy, halo, haloalkyl, nitro, amino, mono- and di-alkylamino, acylamino, carboxy, carboxyalkyl, carbalkoxy, carbaralkoxy, carbalkoxyalkyl, carbalkoxyalkenyl, aminoalkoxy, amido, mono- and di-alkylamido and N,N-cycloalkylamido, phenyl, or benzoyl.

R substituents may contain functional groups such as carboxylic acids, poly(alkoxy)ethers, quaternary ammonium salts, and reactive functional groups. Preferred reactive functional groups are mono- and di-chloro triazine, vinyl sulfone, and vinyl amide.

As employed above and throughout this disclosure, the following terms, unless otherwise indicated, shall be understood to have the following meanings:

"Monocyclic aryl" means a carbocyclic and/or heterocyclic aromatic ring. Preferred rings include phenyl, pyrimidinyl, 1,2,3-triazole. More preferred are s-triazines.

"Bicyclic aryl" means a bicyclic ring system composed of two fused carbocyclic and/or heterocyclic aromatic rings. Preferred rings include naphthyl, indolyl, benzothienyl, benzofuranyl, quinolinyl, chromonyl, 1(2H)-isoquinolonyl, isoquinolinyl, benzimidazolyl, benzothiazolyl, quinoxalinyl, naphthyridinyl, cinnolinyl, phthalazinyl, pyrido[2,3-b]pyrazine, pyrido[3,4-b]pyrazine, pyrido[3,2-c]pyridazine, pyrido [3,4-b]-pyridine, pteridine, and quinazolinyl. Preferred rings include naphthyl and derivatives of 2,3-dichloroquinoxaline.

"Alkyl" means a saturated aliphatic hydrocarbon, or a partially unsaturated aliphatic hydrocarbon, either branched-, straight-chained or cyclic. Preferred "loweralkyl" groups are branched, such as t-butyl and isopentyl. Preferred cyclic alkyl groups are cyclopentane and cyclohexane. Preferred "higheralkyl" groups are substituted or unsubstituted alkyl chains of C8-35 long.

"Alkoxy" refers to an alkyl-O-group. Preferred alkoxy groups are chosen from a list of fatty alcohols such as capryl alcohol, 2-ethyl hexanol, dodecanol, myristyl alcohol, cetyl alcohol, palmitoleyl alcohol, isostearyl alcohol, stearyl alcohol, elaidyl alcohol, oleyl alcohol, linoleyl alcohol, elaidolinoleyl alcohol, linolenyl alcohol, elaidolinolenyl alcohol, ricinoleyl alcohol, arachidyl alcohol, behenyl alcohol, erucyl alcohol, lignoceryl alcohol, sterol, ceryl alcohol, montanyl alcohol, myricyl alcohol, and geddyl alcohol.

"Poly(alkoxy)" refers to linear alcohol ethers such as polyethylene glycol.

"Aryloxy" refers to an aryl-O-group. The preferred aryloxy groups are phenoxy and naphthoxy.

"Aralkyl" means an alkyl group substituted by an aryl radical. The preferred aralkyl groups are benzyl or phenethyl.

The preferred aralkoxy groups are benzyloxy and phenethoxy.

The preferred acyloxy groups are benzoyloxy. Preferred acyloxy groups also include derivatives of unsaturated fatty acids (caprylic, capric, lauric, myristic, palmitic, stearic, arachidic, behenic) and derivatives of saturated fatty acids (myristoleic, palmitoleic, oleic, linoleic, alpha-linoleic, arachidonic, eicosapentaeionic, erucic, docosahexaenoic).

Next we turn to the Y moiety of the general formula. As explained, the problem with food dyes for cosmetic use is that they are water-soluble, which limits their use in cosmetics because they could dissolve in perspiration. To that extent, formulators have been using pigments, which are insoluble, to give color to cosmetics. By adding Y, a large bulky organic molecule can render any dye soluble in either water or oil. Thus, water solubility can be obtained by adding hydrophilic (—OH) groups onto Y, and oil solubility can be obtained by adding hydrophobic alkyl chains onto Y to get solubility in oil-based cosmetics. Thus, a dye may be made soluble only in alcohol or acetone as in Examples 3 and 4 because the alkyl groups present are not long enough for solubility in mineral oil. Lastly, to render the dyes insoluble in water and in greasy, aliphatic oils, one can add phenyl or aryl-rich substituents on Y. For example, compound II of Example 2 with the tetraphenylmethane adduct shows solubility only to dichloromethane and toluene.

The bulky organic substituents also allow the dyes to have photoluminescence because they limit the interaction of the dye with other species in solution that could quench the luminescence. Most dyes fluoresce only in very dilute solution, because there is no quenching. Thus, if one wants a water-soluble dye that fluoresces, one can covalently link it to a cyclodextrin, which is bulky.

More specifically, Y is made up of at least three cyclic rings which may or may not be conjugated. These rings include a plurality of carbocycles, heterocycles, aromatic, heteroaromatic compounds, macrocycles, or combinations thereof. For example, Y may be aromatic as in tetraphenylmethane, tetraphenlysilane, triphenylsilane, triphenylmethylamine, or polyphenylenes. Non-aromatic examples include but are not limited to cyclodextrins and carbosiloxanes or combinations of aromatic and non-aromatic groups such as calixarenes. Preferential Y is a derivative of S-triazine or tetraphenylmethane, due to their ease of synthesis and use as the linking moiety.

While there are a variety of organic structures that can be used for Y, it is critical that substituent Y must exhibit steric bulk, which largely governs the solubility of the dye. For example, it is well known that large polyphenylene dendrimers show poor solubility even in organic solvents. Preferably, the cyclic groups present in Y are not coplanar. This controls the interaction of a dye molecule with its environment, such as in solvents. For example, Y derivatives of tetraphenylmethane are soluble chlorinated solvents but not in water nor in hydrocarbon solvents. Preferably, Y is selected from the group consisting of Tetraphenyl silane, Triphenyl silane, Triphenyl methane, Tetraphenyl methane, Polyphenylene (1,2,3,4-tetraphenylbenzene and 1,2,3,4,5-pentaphenylbenzene), Calixarenes, and Cyclodextrins (alpha, beta, gamma).

The number, Z of Y groups that are present is determined by the available reactive sites within the dye. Moreover, the number of Y may be altered in order to obtain the correct solubility of the dye. For example, X may have six reactive sites, but only three Y's may be attached. The resulting dye may also be a composition of variously substituted compounds of the formula X—$(Y)_Z$, where Z is from 1-10, preferably from 1-6, and most preferred 1-3.

Where there is more than one Y group present, they may or not be the same ($Y_1 \neq Y_2$). However, it is preferable that they are the same ($Y_1 = Y_2$).

As far as the degree of solubility of the compounds of the dye are concerned, water-soluble dyes can become completely insoluble in water after addition of Y. However, their solubility could vary in different organic solvents. More importantly, however, certain Y structures are only soluble in boiling toluene or dichloromethane. These include 1,2,3,4-tetraphenylbenzene, diphenylamine derivatives of triazine, and tetraphenylmethane as in compound II of Example 2. These are useful as far as coloring powders such as mica, kaolin, talc, zinc oxide, etc. because they do not dissolve in oil or water when used in cosmetic compositions. To get solubility in greasy aliphatic oils which are used in cosmetics, one needs to incorporate long aliphatic chains in Y. The point is, the focus is on designing the dye molecule, not encapsulating it, or physically separating until use, or in other techniques that sacrifice color, fluorescence or purity.

Putting these molecules into a cosmetic vehicle requires manipulation of their solubility towards organic solvents or water. To limit the solubility in organic solvents, Y may contain hydrophobic R groups. The choice of chemical groups is dependent upon the application; in certain cases, Y may be functionalized to exhibit a similar chemical composition as the cosmetic vehicle, for example, addition of long alkyl chains promotes an oily consistency, which is ideal for incorporating the dye into waxes. To facilitate water solubility, Y may contain hydrophilic functional groups which include alcohol, nitro, sulfonate, or polyethylene glycol groups. In some instances, polymers may be attached, such as sugars and polypeptides. In some instances, tetra(alkyl) ammonium groups may be preferred.

Additionally, Y may contain chemically reactive R groups. Reactive functional groups are chosen for the attachment of the dyes onto a substrate, for example, mono- or di-chlorotriazine derivatives allow for attachment onto fibers, whereas alkylthiol derivatives allow for attachment onto gold nanoparticles. Y may contain cationic or anionic functional groups which allow electrostatic interactions, for example with keratinous fibers such as hair. The reactive functional groups in Y also allow for attachment onto a polymer network or a glass, such as silicates from the reaction with tetraethylorthosilicate (TEOS).

The personal care or cosmetic composition according to the invention comprises from 0.0001 to 10% by weight, for example from 0.001 to 8% by weight, and especially from 0.005 to 5% by weight based on the total weight of the composition, of the dye described above as well as a cosmetically tolerable carrier or adjuvant which is other than, or in addition to water. While water is cosmetically tolerable, and in most instances will also be present, the phrase "a cosmetically tolerable carrier or adjuvant" is intended to refer to at least one substance other than water that is customarily employed in personal care or cosmetic compositions.

Particle size having average diameters of 0.1 to 60 microns are preferred, for example 5 to 40 and especially 10 to 30 microns give good color properties and elegance.

Depending on the intended use, the preferred average diameters will vary. For example one embodiment of this invention may be a liquid facial cosmetic formulation comprising a fluorescent whitening agent dye as described above and having a preferred particle size range of between 10 and 30 microns. Another embodiment may be a lipstick formulation comprising the fluorescent whitening agent-containing dye microparticles described above having preferred particle sizes of between 1 and 10 microns.

The personal care or cosmetic preparation according to the invention may be formulated as a water-in-oil or oil-in-water emulsion, as an alcoholic or alcohol-containing formulation, as a vesicular dispersion of an ionic or non-ionic amphiphilic lipid, as a gel, or a solid stick. Preferably the cosmetic preparation is in the form of a liquid or cream, but solid powders can be used.

As a water-in-oil or oil-in-water emulsion, the cosmetically tolerable adjuvant contains preferably from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Examples are mineral oil, castor oil, cyclomethicone, dimethicone, dimethicone copolyol, phenyl trimethicone, trimethyl pentaphenyl trisiloxane, caprylic/capric triglyceride, isostearyl stearoyl stearate, octyldodecyl erucate, triisostearyl citrate, triisostearyl trilinoleate, pentaerythrityl tetraisononanoate, isopropyl myristate, isopropyl palmitate, octyl palmitate, diisostearyl malate, diethyl sebacate and diisopropyl adipate.

Cosmetic liquids may contain mono- or polyols such as ethanol, isopropanol, propylene glycol, hexylene glycol, glycerol or sorbitol.

Cosmetic formulations according to the invention may be contained in a wide variety of cosmetic preparations. Especially the following preparations:

- shaving preparations, e.g. aftershave lotions or aftershave creams;
- skin-care preparations, e.g. skin emulsions, multi-emulsions or skin oils and body powders;
- cosmetic personal care preparations, e.g. facial make-up in the form of lipsticks, day creams, facial lotions, and creams; and
- light-protective preparations, such as sun tan lotions, creams and oils, sun blocks and pretanning preparations.

Depending upon the form of the personal care or cosmetic preparation, it will comprise, in addition to the dye described above, further constituents, for example sequestering agents, non-encapsulated or encapsulated colorants, perfumes, thickening or solidifying (consistency regulator) agents, emollients, non-encapsulated or encapsulated UV absorbers, skin-protective agents, antioxidants and preservatives.

The term "perfume" or "fragrance" as used herein refers to odoriferous materials which are able to provide a pleasing fragrance to fabrics, and encompasses conventional materials commonly used in cosmetic compositions to counteract a malodor in such compositions and/or provide a pleasing fragrance thereto. The perfumes are preferably in the liquid state at ambient temperature, although solid perfumes are also useful, particularly cyclodextrin/-perfume inclusion complexes for controlled release. Included among the perfumes contemplated for use herein are materials such as aldehydes, ketones, esters and the like which are conventionally employed to impart a pleasing fragrance to liquid and solid personal care or cosmetic compositions. Naturally occurring plant and animal oils are also commonly used as components of perfumes. Accordingly, the perfumes useful for the present invention may have relatively simple compositions or may comprise complex mixtures of natural and synthetic chemical components, all of which are intended to provide a pleasant odor or fragrance when applied to fabrics. The perfumes used in personal care or cosmetic compositions are generally selected to meet the normal requirements of odor, stability, price and commercial availability. The term "fragrance" is often used herein to signify a perfume itself, rather than the aroma imparted by such perfume.

As a further customary additive, the personal care or cosmetic compositions may also comprise at least one component capable of sequestering properties. Sequestering agents act to sequester (chelate) metal ions. Said sequestering agents may be present at a level of up to 0.5%, more preferably from 0.005% to 0.25%, most preferably from 0.01% to 0.1 wt-%, based on the total weight of the personal care or cosmetic composition.

Compositions according to the invention may be prepared by physically blending X-L-(Y)z as described above containing one or more fluorescent moieties into personal care formulations by methods which are well known in the art. The examples illustrate several such methods.

The X-L-(Y)z molecules according to the invention are able to both scatter and reemit light in a diffuse manner in order to reduce the visual appearance and perception of skin imperfections, such as shadows, skin discolorations, wrinkles and cellulite when applied to at least a part of the body, for example to the surface of the skin. Hence the present invention additionally relates to a method of masking or reducing the appearance of skin imperfections, which comprises applying a solid or liquid personal care or cosmetic formulation having an effective amount of X-L-(Y)z microparticles according to the invention to the surface of the skin.

In one embodiment of the method, the personal care or cosmetic formulation comprises from 0.0001 to 10% by weight, for example from 0.001 to 8% by weight, and especially from 0.005 to 5% by weight based on the total weight of the formulation, of the dye microparticles described above.

In one embodiment of the method, the personal care or cosmetic composition is formulated as a water-in-oil or oil-in-water emulsion, as an alcoholic or alcohol-containing formulation, as a vesicular dispersion of an ionic or non-ionic amphiphilic lipid, as a gel, or a solid stick.

In various embodiments of the method, the personal care or cosmetic composition is in the form of a shaving preparation, a skin-care preparation, a cosmetic personal care preparation or a light-protective preparation.

The powders of the invention are prepared by standard grinding techniques, such as jet milling, roller milling or pulverization. The average particle size of the powders will normally be, for aesthetic reasons, no larger than about 60 microns; preferably the particle size is between 5 and 40 microns and more preferably between about 10 and 20 microns. The amounts of the powders may be varied depending upon the intensity of the fluorescence and color of the mineral, and can be present in an amount of from about 0.01% to about 50%, more preferably, however, the amount used will be between about 0.01% up to about 10%, most preferably about 1% to about 8%, with about 2-5% being the most commonly employed amount.

It may also be desirable to treat the powders to render them more hydrophobic, as the powders normally have a high affinity for binding water. As with more traditional pigments, the powders can be coated with a hydrophobic coating such as metal salts of fatty acids, e.g., magnesium stearate, magnesium myristate, or aluminum stearate.

The powders can be incorporated into any kind of vehicle that is normally used for cosmetic compositions. For example, the minerals can be added to solutions, colloidal dispersions, emulsions (oil-in-water or water-in-oil), suspensions, powders, creams, lotions, gels, foams, mousses, sprays and the like.

In the case of the use of powders in a color cosmetic, the powder dye preferably does not constitute the sole or even the primary colorant for the product. In a color cosmetic, the powder will be typically combined with other pigments or dyes. The additional color components can be either organic or inorganic. Examples of useful inorganic pigments include iron oxides (yellow, red, brown or black), ferric ammonium ferrocyanide (blue), manganese violet, ultramarine blue, chrome oxide (green), talc, lecithin modified talc, zeolite, kaolin, lecithin modified kaolin, titanium dioxide (white) and mixtures thereof. Other useful pigments are pearlants such as mica, bismuth oxychloride and treated micas, such as titanated micas and lecithin modified micas can be used.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

EXAMPLES

Compound IV is a derivative of fluorescein (also known as D&C Yellow No. 8). Dilute solutions of fluorescein absorbs light at 494 nm and emits green light with a maxima at 521 nm. The precursor dye occurs as a red solid that is soluble in water, whereas compound IV is a yellow solid that is not soluble in water. It is also insoluble in mineral oil, but dissolves in acetone, alcohol, and chlorinated solvents.

Compound I is a derivative of toluidine blue O and compound III is a derivative of pararosaniline, which are both water soluble. Both precursor dyes fluoresce in the red end of the spectrum (660-700 nm and 604-627 nm, respectively) which would impart skin a 'red' glow. Compounds I and II are both insoluble in water and in mineral oil, and show solubility in acetone, alcohol, and chlorinated solvents. Pigments of I and II with kaolin appear light blue and magenta, respectively.

Compound II is a stilbene derivative, and 4,4'-diaminostilbene absorbs light in the Cyanuric chloride (1.62 g) was dissolved in tetrahydrofuran (10 mL) and DIPEA (1.53 mL) and cooled in an ice-water bath. While stirring, capryl alcohol (1.39 mL) was added slowly. After stirring for 2 h, additional DIPEA (1.53 mL) was added and the ice bath removed. Two-thirds of the solution was used to make Compound I, and the remaining one-third was used to make Compound II:

Example 1

(Compound I)

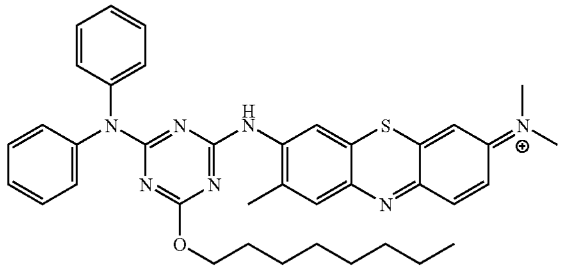

N-(7-(4-(diphenylamino)-6-(octyloxy)-1,3,5-triazine-2-ylamino)-8-methyl-3H-phenothiazin-3-ylidene)-N-methylmethanaminium Two-thirds of the above solution was added to a 50-mL round-bottomed flask containing diphenylamine (0.99 g). The solution was stirred overnight at room temperature. Toluidine blue (1.58 g) was added, along with additional DIPEA (1 mL). After stirring for 4 h, acetonitrile (10 mL) was added and the mixture was heated to reflux overnight. The resulting solution was cooled and partitioned between water and methylene chloride. The organic solvent was evaporated, and the residue was dissolved in acetone. Water was added to induce a blue precipitate, which was filtered. The product is also soluble in methanol, but insoluble in water.

A small amount of the product was dissolved in acetone (10 mg in 20 mL), which was slowly added to kaolin (10 g). The solution was heated to 30° C. and the solvent allowed to slowly evaporate with mixing. The resulting powder is light blue, and stable in oil and in water.

Example 2

(Compound II)

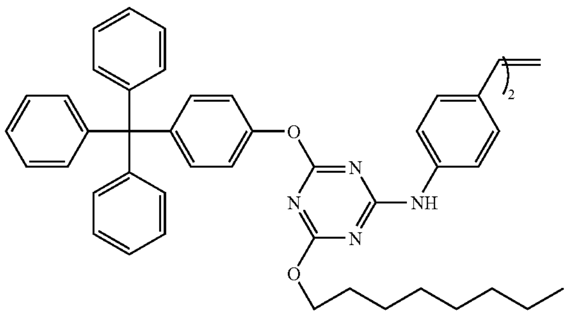

(E)-4,4'(ethene-1,2-diyl)bis(N-(4-(octyloxy)-6-(4-tritylphenoxy)-1,3,5-triazine-2-yl)benzenamine One-third of the above solution was added to a 25-mL round-bottomed flask containing 4-tritylphenol (0.986 g). The resulting solution was stirred overnight at room temperature before adding 4,4'-diaminostilbene dihydrochloride (207.2 mg) and additional DIPEA (3 mL). The mixture was heated to reflux overnight, and then cooled. Methanol (3 mL) was added and the mixture filtered, and washed with more methanol. The precipitate was dissolved in hot dichloromethane and hot filtered. Precipitation of the product was induced by adding methanol to the filtrate solution. The solid was collected by vacuum filtration, and washed further with methanol to give a cream solid. The solid was insoluble to common organic solvents, except for hot dichloromethane and toluene.

A small amount of the product was dissolved in methylene chloride (50 mg in 25 mL) by warming and sonication. This solution was slowly added to a slurry of kaolin in methylene chloride (5 g in 10 mL). The solution was heated to 30° C. and the solvent allowed to evaporate with mixing. The resulting white powder looks similar to the kaolin starting material, but fluoresces blue under a UV 254 lamp.

Example 3

(Compound III)

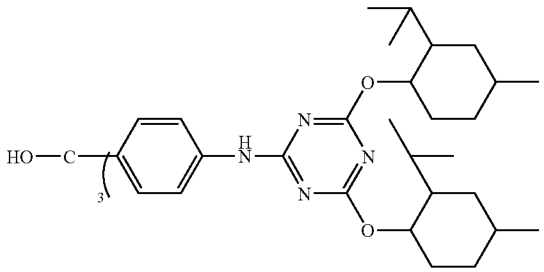

tris(4-(4,6-bis(2-isopropyl-4-methylcyclohexyloxy)-1,3,5-triazine-2-ylamino)phenyl)methanol A round-bottomed flask containing a solution of cyanuric chloride (1.67 g) in tetrahydrofuran (10 mL) was cooled in an ice-water bath. Diisopropylethylamine (3.15 mL) was added, followed by the portion wise addition of menthol (2.83 g). The ice bath was removed and the solution was stirred overnight. To the resulting orange slurry was added pararosaniline (830 mg) and additional DIPEA (6 mL). The mixture was heated to reflux overnight, cooled, and diluted with methylene chloride. The solution was washed thrice with water, then with brine, and then dried over sodium sulfate and then filtered to remove the solids, which included unreacted starting material. Evaporation of the solvent gave an oil, which was further purified with a short silica plug using dichloromethane. The product was removed from the column by the addition of acetone. Evaporation gave a purple solid.

A small amount of the product was dissolved in methylene chloride (50 mg in 30 mL), which was slowly added to kaolin (5 g). The suspension was heated to 30° C. and the solvent allowed to slowly evaporate with mixing. The resulting powder is purple and stable in water and in mineral oil.

Example 4

(Compound IV)

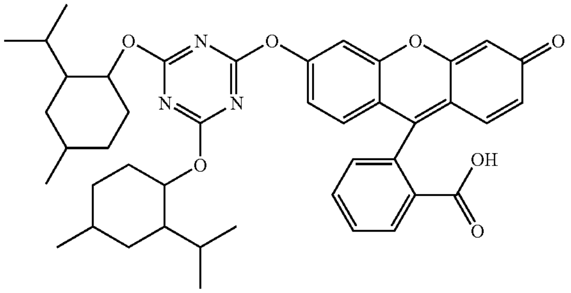

2-(3-(4,6-bis(2-isopropyl-4-methylcyclohexyloxy)-1,3,5-triazine-2-yloxy)-6-oxo-6H-xanthen-9-yl)benzoic acid Acetone (5 mL) mixture of cyanuric chloride (1 g) and potassium carbonate (1.5 g) in a 50-mL round-bottomed flask. The suspension was cooled in an ice-water bath before adding menthol (1.69 g) portion wise. After 5 min, the ice bath was removed and the mixture stirred overnight with a bubbler. Ice (5 g) was added to the resulting bubbler, followed by fluorescein (1.80 g) and additional potassium carbonate (1.5 g). The mixture was heated to reflux overnight. The biphasic solution was cooled and extracted with methylene chloride, before drying over sodium sulfate, filtering, and evaporating to get a yellow oil. A short silica column was used to further purify the product, by eluting with 1:3 acetone in methylene chloride.

A small amount of the product was dissolved in methylene chloride (50 mg in 5 mL), which was slowly added to a slurry of kaolin in methylene chloride (5 g in 10 mL). The solution was heated to 30° C. and the solvent allowed to evaporate with mixing in a rotavap. The resulting powder shows a slight tint of yellow, and fluoresces yellow-green under a UV 254 lamp.

Example 5

Formulation

Oil-in Water Cream Containing 0.04% of Compounds 1-1V

| PHASE | INGREDIENT | CONTROL CREAM AMOUNT [WT-%] | TEST CREAM AMOUNT [WT-%] |
|---|---|---|---|
| A | Deionized Water | 82.95 | 80.95 |
| | Hydroxyethylcellulose | 0.70 | 0.70 |
| | Methylparaben, USP | 0.30 | 0.30 |
| B | $C_{12}$-$C_{15}$ Alkyl Octanoate | 3.00 | 3.00 |
| | Trioctyldodecyl Citrate | 2.00 | 2.00 |
| | Ethylhexyl Palmitate | 3.00 | 3.00 |
| | Glyceryl Stearate | 1.00 | 1.00 |
| | Stearic Acid | 2.00 | 2.00 |
| | Sorbitan Oleate | 0.80 | 0.80 |
| | Polysorbate 80 | 0.15 | 0.15 |
| | Propylparaben, USP | 0.10 | 0.10 |
| C | Deionized Water | 2.00 | 2.00 |
| | Triethanolamine | 0.70 | 0.70 |
| D | Compounds I-IV | 0.00 | 2.00 |
| E | Deionized Water | 1.00 | 1.00 |
| | Diazolidinyl Urea | 0.30 | 0.30 |

In a suitable vessel the water and the hydroxyethylcellulose of phase A are mixed using a homogenizer for 60 minutes and heated to 75-80° C. Then the methyl paraben of phase A is added and mixed for about 5 minutes, maintaining the same temperature as above. The ingredients of phase B are premelted at 75-80° C. and mixed in a separate vessel. When a uniform liquid solution is obtained phase B is added to phase A using high-speed homogenizer. The emulsion is homogenized for 15-20 minutes at 75-80° C. Phase C is added to the vessel while using the homogenizer. The heating process is stopped and the mixture is allowed to gradually cool down. At 60-65° C. phase D is added using a lightning mixer. At 45° C. phase E is added to the vessel. The mixing is stopped when room temperature is achieved. This results an O/W cream with good overall properties.

Example 6

Formulation

Liquid Makeup—Oil-in-Water Foundation

| PHASE | INGREDIENT | AMOUNT [WT-%] |
|---|---|---|
| A | Deionized Water | 53.88 |
| | Sodium Hydroxide 10% solution | 1.30 |
| | Dimethicone Copolyol | 0.10 |
| B | 80% Titanium Dioxide/Talc | 7.50 |
| | 80% Yellow Iron Oxide/Talc | 2.25 |
| | 80% Red Iron Oxide/Talc | 1.38 |
| | 80% Black Iron Oxide/Talc | 0.25 |
| | Talc | 0.72 |
| C | Butylene Glycol | 4.00 |
| | Magnesium Aluminum Silicate | 1.00 |
| D | Butylene Glycol | 2.00 |
| | Cellulose Gum | 0.10 |
| E | Methylparaben | 0.10 |
| F | Di-PPG-3 Myristyl Ether Adipate | 14.00 |
| | Dioctyl Maleate | 4.00 |
| | Steareth-10 | 2.00 |
| | Steareth-2 | 0.50 |
| | Cetyl Alcohol | 0.62 |
| | Dicetyl Phosphate, Ceteth-20 Phosphate Cetearyl Alcohol | 4.00 |
| | Propylparaben | 0.10 |
| G | Compounds I-IV | 0.02 |
| H | DMDM Hydantoin | 0.18 |
| | TOTAL | 100.00 |

From the above examples 1-6, it can be see that the invention accomplishes at least all of the inventor's primary objectives.

The following claims are intended to encompass the full scope of the invention including the area beyond the claims which comes within inventor's legally entitled scope of equivalency.

What is claimed is:

1. The Compound I, N-(7-(4-(diphenylamino)-6-(octyloxy)-1,3,5-triazine-2-ylamino)-8-methyl-3H-phenothiazin-3-ylidene)-N-methylmethanaminium of the formula:

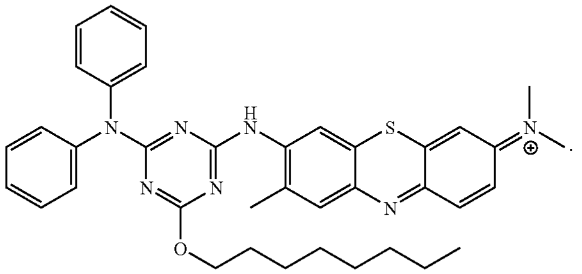

2. The Compound II, (E)-4,4'-(ethene-1,2-diyl)bis(N-(4-(octyloxy)-6-(4-tritylphenoxy)-1,3,5-triazine-2-yl)benzenamine) of the formula:

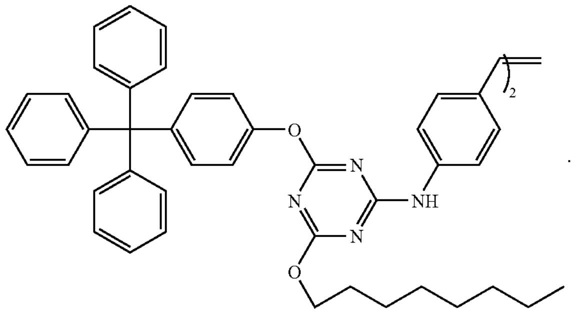

3. The Compound III, tris(4-(4,6-bis(2-isopropyl-4-methylcyclohexyloxy)-1,3,5-triazine-2-ylamino)phenyl)methanol of the formula:

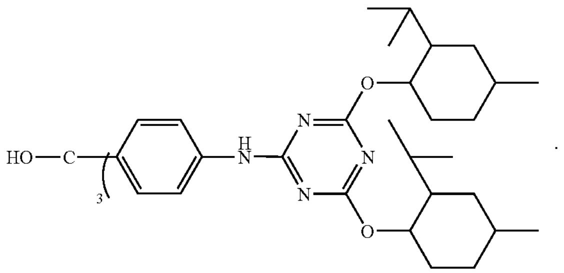

4. The Compound IV, 2-(3-(4,6-bis(2-isopropyl-4-methylcyclohexyloxy)-1,3,5-triazine-2-yloxy)-6-oxo-6H-xanthen-9-yl)benzoic acid of the formula:

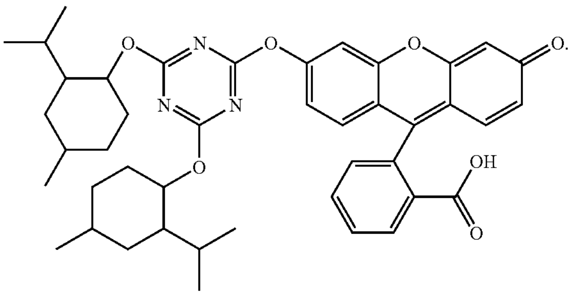

* * * * *